(12) United States Patent
Schneider

(10) Patent No.: US 6,296,841 B1
(45) Date of Patent: Oct. 2, 2001

(54) ODOR CONTROL COMPOSITION AND PROCESS

(75) Inventor: David J. Schneider, Union, KY (US)

(73) Assignee: H & S Chemical Co., Inc., Covington, KY (US)

( * ) Notice: Subject to any disclaimer, the term of this patent is extended or adjusted under 35 U.S.C. 154(b) by 0 days.

(21) Appl. No.: 09/477,318

(22) Filed: Jan. 4, 2000

(51) Int. Cl.$^7$ ................................. A61L 9/00; A61L 9/01
(52) U.S. Cl. ..................... 424/76.1; 424/762; 424/76.21; 424/76.5; 424/76.6; 424/76.7
(58) Field of Search .................................. 424/76.1, 76.2, 424/76.22, 76.21, 76.4, 76.8

(56) References Cited

U.S. PATENT DOCUMENTS

| | | | |
|---|---|---|---|
| 4,594,239 | 6/1986 | Pluim, Jr. .............................. | 424/10 |
| 4,619,710 | 10/1986 | Kuenn et al. ...................... | 134/22.17 |
| 5,164,106 | * 11/1992 | Ahmed et al. ....................... | 252/104 |
| 5,846,418 | 12/1998 | Thompson et al. .................. | 210/266 |

OTHER PUBLICATIONS

Chluramine T By. D H Bremner Chapter 1.

* cited by examiner

*Primary Examiner*—Shelley A. Dodson
(74) *Attorney, Agent, or Firm*—Donald R. Bahr

(57) ABSTRACT

The disclosure of this invention relates to odor control and more particularly, to a process and composition whereby household and institutional odors are eliminated wherein these odors are incorporated in a variety of substrates. The odor composition of this invention is a solution of Chloramine-T and a suitable wetting agent. The solutions in this invention may further be buffered. The concentration of the Chloramine-T can be from about 0.5 to about 10 weight percent. The concentration of the wetting agent can be from about 0.1 to about 5%.

21 Claims, No Drawings

ODOR CONTROL COMPOSITION AND PROCESS

FIELD OF THE INVENTION

This invention is concerned with odor control technology and more particularly with household and institutional odor control. In accordance with this invention, odors attributed to a wide variety of human and animal endeavors can be controlled or eliminated. The odor control process of this invention comprises the application of a solution of the odor control composition of this invention to the odor containing substrate.

BACKGROUND OF THE INVENTION

The application of materials and solutions to substrates for purposes of odor control is common and in fact is thousands of years old, in the most common situation solutions or materials with a pleasant odor are applied to a substrates, for example, to furniture or carpets. In the past the most common method of odor control was to apply solutions which are perfumes to the odor containing substrate. These perfumes did not control the odor but only masked the odor. That is in the prior art the odor was not controlled but instead it was only masked. In contrast in accordance with the subject invention the troublesome odors are not just masked but instead they are chemically controlled or eliminated. This end is effected by treating the substrate with a solution which contains Chloramine-T. To some degree the use of Chloramine-T for odor control is known in the prior art however the use of the composition and process of this invention is not known. With this invention it is possible to eliminate odors resulting from a wide range of sources such as smoking, animal and human fluids, mildew, cooking etc. In its broadest terms, this invention relates to the utilization of a particular Chloramine-T solution which reacts with odor producing molecules as may be contained in a substrate.

BRIEF DESCRIPTION OF THE INVENTION

Odor control has been a problem which man has addressed for thousands of years, scented or perfumed compositions for odor control are well known in the prior art. Regardless of the widespread usage of these compositions, the problem of effective odor control remains a common and troublesome problem. This situation results from the fact that the prior art solutions do not control the odorous materials as may be in the substrate. The composition and related process of this invention react with the odorous materials are contained in the substrate and thereby eliminate the same.

The subject invention is concerned with a means whereby undesirable odors in a substrate can be eliminated by use of the active chlorine in Chloramine-T to react with the odorous material on a molecular level.

In the preferred embodiment, the odor controlling solution for use in this invention incorporates Chloramine-T, a wetting agent and a buffering agent. Using the composition and process of this invention odors in the substrate are eliminated because the odor controlling solution wets out the substrate allowing the active chlorine moiety to react with the odorous molecules. The odor controlling composition comprises a solution of Chloramine-T which contains a wetting agent which is compatible with the Chloramine-T. The wetting agent must not degrade the active chlorine in the Chloramine-T. Preferred wetting agents are generally anionic. In other words the wetting agent in the odor control solution does not degrade the active Cl+ moiety which is formed when Chloramine-T goes into solution. If the Cl+ moiety is degraded the Chloramine-T is less effective as an odor control agent.

DESCRIPTION OF THE PREFERRED EMBODIMENT

In accordance with the above discussion this invention is concerned with a process for controlling odors in household and institutional applications. Perfumed odor control compositions have been used for thousands of years however these solutions did not destroy the odorous materials but instead they only mask the odors caused by these materials. In contrast to this masking of the troublesome odorous material in the prior art, the composition and process of this invention reacts with the odorous molecules. In the prior art odor control compositions are perfumes wherein the odors are masked with synthetic or natural essence. In the subject invention, instead of masking the odor with a perfume, the odor causing molecules are degraded by reaction with the Cl+ moeity and with the chemical moeity which remains after the Cl+ moeity is removed from Chloramine-T. The use of Cl+ is common in odor control, the most common Cl+ producing composition is household bleach. The preferred source of a Cl+ moeity for use in accordance with this invention is Chloramine-T.

Chloramine-T is a common trivial name used to describe a variety of compounds which are based on N-Sodium, N-Chloro-Par-Toluenesulfonamide and N-Sodium, N-Chloeo-Par-Benzenesulfonamide. The preferred Chloramine-T for use in this invention is a tri hydrated sodium salt. As is mentioned above bleach has been commonly used as a source of Cl+ cations which are useful as deodorizers. Because of the problems associated with the use of bleach, i.e. the discoloration of the substrate, it is generally not suitable for use as a deodorizer. In addition the Cl+ cation which is produced by bleach is much more ionic when compared to the Cl+ cation produced by Chloramine-T. That is when compared to the Cl+ cation produced by bleach the Cl+ cation produced Chloramine T is much more covalent. As a result of this covalence the side effects produced by the Cl+ cation produced by Chloramine-T are not as severe as those produced by bleach. As a result the Cl+ cation produced by Chloramine-T can be used to deodorize as it does not have side effects such as a strong bleach smell, the undesirable bleaching of the odor containing substrate etc. Further Chloramine-T is more stable than bleach and has a higher Cl+ activity than bleach.

Further when compared to bleach Chloramine-T is a superior deodorizing agent as the chemical moiety, the backbone, remaining after the Cl+ cation is released by Chloramine-T, further reacts with the odor containing molecule thereby permanently removing it as a potential source of odor. In contrast the chemical moiety which remains after the Cl+ cation is removed from bleach has no ability to react with odor causing molecules.

Most odor causing molecules are mercaptans sulfides or amines. Chloramine-T is an excellent agent to eliminate odors which are mercaptan, sulfide or amine based as both the Cl+ cation produced by Chloramine-T and the residual chemical moiety remaining after the Cl+ cation is produced, react with the odor causing molecule.

In order for Chloramine-T to be effective it must come into contact with the substance which is responsible for the odor. If the substance which is responsible for the odor is in an environment which makes access difficult i.e. pet stains in a carpet, a means must be provided for bringing the Chloramine-T into contact with the odor causing substance. In many instances when aqueous solution is used as the delivering medium the solution tends to bead up on the substrate. Therefore, when the water component of the solution evaporates the substance in solution is deposited only in localized areas. In the case at hand if an aqueous solution of Chloramine-T were applied to a carpet containing pet stains, the solution would bead up on the carpet, such that when the water evaporated the placement of the Chloramine-T on the carpet would be spotty. Due to this placement the two reactive components of the Chloramine-T would not be in position to react with all of the odor causing substance on a molecular basis. That is the reaction of the Chloramine-T with the pet stain would be incomplete, and hence the odor control would be incomplete.

The use of wetting agents with various solutions in order to reduce surface tension is common in the prior art. For example wetting agents are commonly added to herbical solutions to allow the herbicide to wet out plant leaves Likewise the use of wetting agents with insecticides is common.

In accordance with this invention a substance is added to the Chloramine-T solution to reduce the surface tension of the solution. As is discussed above Chloramine-T functions in part by the reaction of the Cl+ moiety with the odor causing molecule. This invention is concerned with the fact that many substances which are suitable for reducing the surface tension of the solution adversely affect the formation of the Cl+ moiety, from Chlormaine-T or degrade said Cl+ moiety once it is formed.

Suitable substances which are useful in accordance with this invention for reducing the surface tension of the Chlormaine-T solution, are synthetic and natural wetting agents. Wetting agents are generally classified as cationic anionic, amphoteric and nonionic. Because there are thousands of natural and synthetic wetting agents it is impossible to make generalizations as to which would be effective in the composition of this invention. With this caveat it can be said that generally the most preferred wetting agents for use in accordance with this invention are anionic wetting agents, with the next preferred class of wetting agent being a nonionic wetting agents. Amphoteric and cationic wetting agents are least preferred for use with the composition and process of this invention.

Regardless of the above comments satisfactory wetting agents may be found in any class of wetting agents.

While the applicant is not sure of all ramifications of how different wetting agents degrade the Cl+ moiety it is felt that functional groups such as alkenes, alcohol, ketone, phenols as may be contained on the base molecule are particularly harmful to the Cl+ moiety. Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols.

The concentration of the wetting agent used in accordance with this invention can be from about 0.1 to 5%. A more preferred concentration for the wetting agent is from about 0.5 to about 1.5%. In order to achieve maximum efficiency in the odor control process the surface tension of the solution must be reduced so that Chloramine-T can reach and act with the odor causing molecules.

A factor in choosing the concentration of the wetting agent is the degree to which it foams. If undesirable foaming occurs anti foamers may be added to the solution.

For stability and for optimum function ability as an odor killing agent the pH of a solution of Chloramine-T should be between 7–10, with a more preferred pH range being between 8–9.5 with a most preferred range being between 8.5–9.

A 5% solution of Chloramine-T naturally buffers itself at a range of about 8.5–9.5. In order to maintain the Chloramine T solution in accordance with these pH ranges it is preferred that the Chloramine-T solution be buffered. The buffering of the Chloramine-T solution further compensates for any change in pH that may result from the acidity of the water which is used to make the solution, the conditions of application, the type of substrate, and the nature of the odor causing molecule.

Buffering agents which are suitable for use in accordance with this invention are sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate and mixtures thereof.

Because of price, ease of use, low toxicty and their effect on the environment, the above listed sodium and potassium bicarbonate are preferred buffering agents for use in this invention. Buffered solutions are advantageous in that the active ingredients of the odor control solution of this invention can be shipped in powdered form and mixed by the consumer with no adverse effects.

The concentration of the buffer can be from 0% up to the limit of solubility. The preferred range for the concentration of the buffering agent is from about 5% to about 200% of the Chloramine-T in solution. A more preferred range is from about 5% to about 50% with a most preferred concentration being 100%.

Chloramine-T has a limit of solubility of about 15% at room temperature in water. However, for shipping in North America it is preferred that the concentration be 10% or less in order to prevent the Chloramine-T from coming out of solution during transport.

For the industrial odor control it is preferred that the concentration of Chloramine-T be about 5–10%. For residential consumer use the concentration of Chloramine-T can be from about 0.25 to about 2.0%, with a more preferred range being from about 0.5 to about 1.0% percent, with the most preferred concentration being 0.75%. These lower concentrations keep the bleach like smell to a minimum but still gives the desired odor control.

Chloramine-T is the preferred source of the Cl+ moiety for use in odor control in this invention. However another suitable source the Cl+ moiety is Chloramine-B.

EXAMPLES

The present invention is illustrated by the following Examples which are not to be constructed as limiting the invention to their details.

1. After a fire the air transfer ducts in a building were contaminated with a strong smoke odor which was transferred to air moving through the duct work. The building occupants found the smell of the air to be objectionable. The inside of the duct work was treated with an aqueous solution containing 0.75% Chloramine-T and 50% of dodecylbenzene sulfonic acid. The treatment was affected by atomizing the solution directly into the cold air return ducts. The furnace fan was then activated in order to spread the atomized solution throughout the duct work. In thirty minutes the smoke odor was eliminated.

2. The locker room, showers and workout areas of a health club smelled of human perspiration. These odors had proved to be impossible to eliminate using prior art odor control solutions. The solutions of Example 1 was misted throughout the odorous area at a height of about 6 ft. above floor level. The perspiration odors were eliminated in a matter of minutes.
3. The inside of a used automobile had a strong tobacco smoke odor as a result of the previous owners smoking. After the automobile was traded in, the used car department of the automobile dealer tried to eliminate the smoke odor by spraying the inside of the automobile with an orange scented solution, in an attempt to mask the smoke odor. A subsequent owner of the automobile found the orange-tobacco smoke odor, which permeated the inside of the car to be objectionable. The whole inside of the car was sprayed with the solution of Example 1, as a result of this spraying the orange-tobacco smoke odor on the inside of the car was eliminated in approximately thirty minutes.
4. The carpet in the salad bar area of a restaurant emitted a strong, old or rotten, food odor. The carpet was vacuumed and the solution of Example 1 was applied to the area with a spray mist bottle. The odors were eliminated and did not return.
5. The inside of a mobile home which had been left closed for a considerable period of time had a stale odor. The inside of the mobile home was sprayed with the solution of Example 1. The stale smell was totally eliminated in about one hour.
6. A carpet cleaning company encountered a problem piece of carpet which exhibited the strong smell of cat urine. The carpet was sprayed with the solution of Example 1 and allowed to sit. The carpet was then cleaned and sprayed again with the solution of Example 1. The cat urine odor was eliminated and it did not return.
7. A skunk entered a residential basement and contaminated a basement and the furniture therein. The entire basement and the furniture was sprayed with the composition of Example 1. After thirty minutes the odor was gone.
8. Camping bedding gear was accidentally contaminated with motor oil. The bedding gear was washed however after washing the strong smell of motor oil persisted. The bedding gear was sprayed with the solution of Example 1. After approximately twenty minutes the motor oil smell was gone.
9. A zoo at a major city suffered major fire damage to a pavilion and an adjacent lodge. The adjacent areas were permeated with smoke and exhibited a strong smoke odor. The adjacent area including the floors, walls ceilings, furniture etc were sprayed with the composition of Example 1, except that the concentration of Chloramine-T was 1.25% and the concentration of the wetting agent was 1.00%. After a period of one hour the smoke odor was gone.

In summary, the date of Examples 1 through 9 demonstrates that by use of the odor control composition and process of the subject invention, many common odors can be eliminated.

The foregoing constitutes a description of various features of a preferred embodiment. Many changes to the preferred embodiment are possible without departing from the spirit and scope of the invention. Therefore, the scope of this invention should be determined with reference not to the preferred embodiment but to the following claims.

What is claimed is:

1. A process for controlling odor on a substrate which comprises the steps of: applying a solution containing an effective amount of Chloramine-T to the substrate wherein the solution further incorporates an effective amount of a wetting agent which essentially does not react with Chloramine-T.

2. The process of claim 1 wherein the concentration of the Chloramine-T is from about 0.5 to about 10 weight percent.

3. The process of claim 1 wherein the concentration of Chloramine-T is from about 0.25 to about 2 weight percent.

4. The process of claim 1 whereas the concentration of Chloramine-T is about 0.75 weight percent.

5. The process of claim 1 wherein the wetting agent is a anionic or nonionic wetting agent.

6. The process of claim 2 wherein the wetting agent is a anionic or nonionic wetting agent.

7. The process of claim 3 wherein the wetting agent is a anionic or nonionic wetting agent.

8. The process of claim 4 wherein the wetting agent is a anionic or nonionic wetting agent.

9. The process of claim 1 wherein the wetting agent is an anionic wetting agent.

10. The process of claim 2 wherein the wetting agent is an anionic wetting agent.

11. The process of claim 1 wherein the concentration of the wetting agent is from about 0.1 to about 5 weight percent.

12. The process of claim 3 wherein the concentration of the wetting agent is from about 0.1 to about 5 weight percent.

13. The process of claim 5 wherein the concentration of the wetting agent is from about 0.1 to about 5 weight percent.

14. The process of claim 5 wherein the concentration of the wetting agent is from about 0.5 to about 1.5 weight percent.

15. The process of claim 6 wherein the concentration of the wetting agent is from about 0.5 to about 1.5 weight percent.

16. The process of claim 7 wherein the concentration of the wetting agent if from about 0.5 to about 1.5 weight percent.

17. The process of claim 8 wherein the concentration of the wetting agent is from about 0.5 to about 1.5 weight percent.

18. The process of claim 1 wherein the solution is buffered to a pH of from about 7 to about 10.

19. The process of claim 5 wherein the solution is buffered to a pH of from about 8 to about 9.5.

20. The process of claim 12 wherein the solution is buffered with sodium bicarbonate to a pH of from about 8.5 to about 9.

21. A process for controlling odor on a substrate which comprises applying an aqueous solution which contains 0.75 weight percent of Chloramine-T and 0.50 weight percent of dodecyl benzene sulfonic acid to the substrate wherein the pH of the solution is from about 8.5 to about 9.

* * * * *